United States Patent
Saito et al.

(10) Patent No.: US 10,730,852 B2
(45) Date of Patent: Aug. 4, 2020

(54) METHOD FOR PRODUCING 5-ALKYNYL PYRIDINE COMPOUND

(71) Applicant: Nissan Chemical Corporation, Chuo-ku (JP)

(72) Inventors: Hirohisa Saito, Funabashi (JP); Shinji Iba, Funabashi (JP); Yukiko Ebihara, Funabashi (JP)

(73) Assignee: Nissan Chemical Corporation, Chuo-ku (JP)

( * ) Notice: Subject to any disclaimer, the term of this patent is extended or adjusted under 35 U.S.C. 154(b) by 0 days.

(21) Appl. No.: 16/441,753

(22) Filed: Jun. 14, 2019

(65) Prior Publication Data

US 2019/0382372 A1    Dec. 19, 2019

(30) Foreign Application Priority Data

Jun. 15, 2018    (JP) ................. 2018-114439

(51) Int. Cl.
*C07D 401/12*    (2006.01)

(52) U.S. Cl.
CPC ................... *C07D 401/12* (2013.01)

(58) Field of Classification Search
CPC ................................... C07D 401/12
See application file for complete search history.

(56) References Cited

U.S. PATENT DOCUMENTS

| 4,434,182 A | 2/1984 | Cruickshank et al. |
| 10,029,986 B2 * | 7/2018 | Mita ............. A01N 43/60 |
| 2011/0105794 A1 | 5/2011 | Zierke et al. |

FOREIGN PATENT DOCUMENTS

| JP | 2017-137283 A | 8/2017 |
| WO | WO 2014/010737 A1 | 1/2014 |
| WO | WO 2015/125824 A1 | 8/2015 |
| WO | WO 2017/208267 A1 | 12/2017 |
| WO | 2018003924 | * 4/2018 |

OTHER PUBLICATIONS

U.S. Appl. No. 16/484,337, filed Aug. 7, 2019, U.S. Pat. No. 2019-0367479-A1, Daisuke Tanima, et al.
Parpart, S. et al. "Synthesis of Unsymmetrical Aza-Ullazines by Intramolecular Alkynyl-Carbonyl Metathesis", Organic Letters, vol. 20, issue 1, 2018, pp. 122-125.

* cited by examiner

*Primary Examiner* — D Margaret M Seaman
(74) *Attorney, Agent, or Firm* — Oblon, McClelland, Maier & Neustadt, L.L.P.

(57) ABSTRACT

To provide an industrial method for producing a 5-alkynyl pyridine compound at a high yield.
A method for producing a compound represented by the formula (3), which comprises reacting a 5-chloropyridine compound represented by the formula (1) and an alkyne compound represented by the formula (2) by using sodium carbonate or sodium hydrogen carbonate in the presence of a palladium catalyst having phosphine ligands:

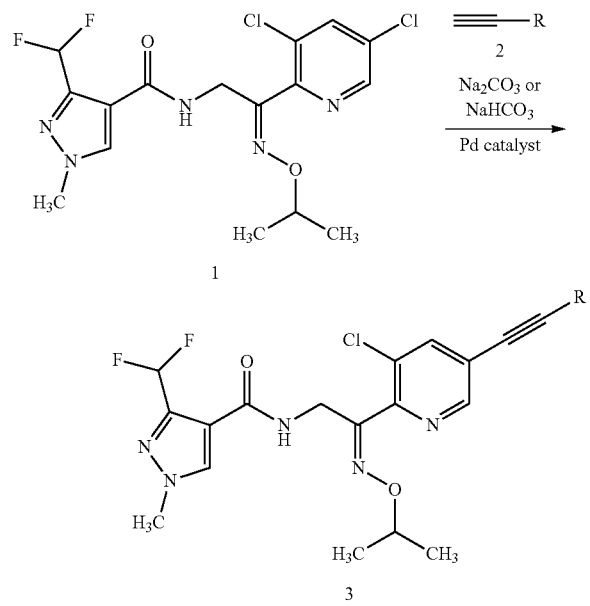

(in the formula (2), R is a hydrogen atom, a $C_1$-$C_6$ alkyl or a $C_3$-$C_7$ cycloalkyl).

15 Claims, No Drawings

METHOD FOR PRODUCING 5-ALKYNYL PYRIDINE COMPOUND

TECHNICAL FIELD

The present invention relates to a method for producing a 5-alkynyl pyridine compound which is useful as an agricultural and pharmaceutical chemical or as an intermediate thereof.

BACKGROUND ART

It is known that some compounds having an alkynylpyridinyl group have biological activity (for example Patent Document 1), and it is also known that among them, an oxime-substituted amide compound having a 5-alkynylpyridinyl group has fungicidal activity (for example Patent Document 2). Further, for example, as described in Patent Document 3, Patent Document 4 and Non-Patent Document 1, a method for introducing an alkynyl group into a pyridine ring is known.

PRIOR ART DOCUMENTS

Patent Documents

Patent Document 1: WO2017/208267
Patent Document 2: WO2014/010737
Patent Document 3: WO2015/125824
Patent Document 4: JP-A-2017-137283

Non-Patent Document

Non-Patent Document 1: Organic Letters, 2018, volume 20, issue 1, page 122,

DISCLOSURE OF INVENTION

Technical Problem

As a method for synthesizing an oxime-substituted amide compound having a 5-alkynylpyridyl group by a coupling reaction with a metal catalyst, for example, a method of using an oxime-substituted amide compound having a 5-bromopyridinyl group described in Patent Document 2 is known. However, a 5-bromopyridine compound is expensive in many cases and is thereby inappropriate for industrial use. On the other hand, an oxime-substituted amide compound having a 5-chloropyridinyl group is inexpensive, however, the reactivity of the chloro group is lower than that of the bromo group. Thus, the development of a novel production method has been desired.

Solution to Problem

The present inventors have studied in order to accomplish the above object. As a result, they have found an industrial method for producing an oxime-substituted amide compound having a 5-alkynylpyridinyl group at a high yield from an oxime-substituted amide compound having a 5-chloropyridinyl group, by using sodium carbonate or sodium hydrogen carbonate as a base, and accomplished the present invention.

That is, the present invention relates to the following features.
[1] A method for producing a 5-alkynyl pyridine compound represented by the formula (3):

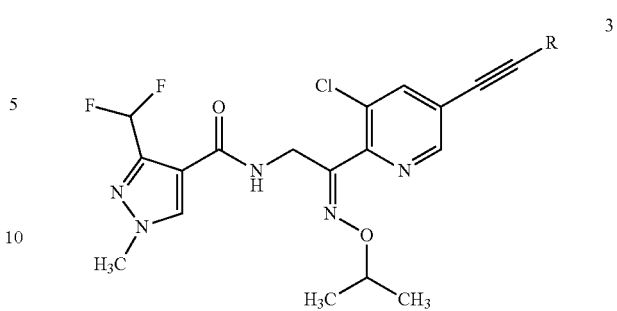

wherein R is a hydrogen atom, a $C_1$-$C_6$ alkyl or a $C_3$-$C_7$ cycloalkyl, which comprises reacting a 5-chloropyridine compound represented by the formula (1):

and an alkyne compound represented by the formula (2):

$$\equiv\!\!-\!\!R$$

wherein R is the same as defined above, by using sodium carbonate or sodium hydrogen carbonate in the presence of a palladium catalyst having phosphine ligands in a solvent.
[2] The method for producing a 5-alkynyl pyridine compound according to the above [1], wherein the 5-chloropyridine compound and the alkyne compound are reacted in the presence of a copper catalyst and the palladium catalyst having phosphine ligands.
[3] The method for producing a 5-alkynyl pyridine compound according to the above [1] or [2], wherein the phosphine ligand is 1,4-bis(diphenylphosphino)butane or 4,5-bis(diphenylphosphino)-9,9-dimethylxanthene.
[4] The method for producing a 5-alkynyl pyridine compound according to the above [1] or [2], wherein the palladium catalyst having phosphine ligands is tetrakis(triphenylphosphine)palladium(0), bis(tri-t-butylphosphine)palladium(0), bis(tricyclohexylphosphine)palladium(0), bis[1,2-bis(diphenylphosphino)ethane]palladium(0), bis(tricyclohexylphosphine)palladium(0), dichlorobis(triphenylphosphine)palladium(II), bis(triphenylphosphine)palladium(II) diacetate, dichloro[1,2-bis(diphenylphosphino)ethane]palladium(II), dichloro[1,1'-bis(diphenylphosphino)ferrocene]palladium(II), dichloro[1,3-bis(diphenylphosphino)propane]palladium(II) or dichlorobis(tri-o-tolylphosphine)palladium(II).
[5] The method for producing a 5-alkynyl pyridine compound according to the above [4], wherein the palladium catalyst having phosphine ligands is dichlorobis(triphenylphosphine)palladium(II).
[6] The method for producing a 5-alkynyl pyridine compound according to any one of the above [2] to [5], wherein the copper catalyst is copper(I) chloride, copper(I) bromide, copper(I) iodide or copper(I) acetate.

[7] The method for producing a 5-alkynyl pyridine compound according to the above [6], wherein the copper catalyst is copper(I) iodide.

[8] The method for producing a 5-alkynyl pyridine compound according to any one of the above [1] to [7], wherein from 0.01 to 20 molar equivalent of the alkyne compound is reacted per the 5-chloropyridine compound.

[9] The method for producing a 5-alkynyl pyridine compound according to any one of the above [1] to [8], wherein from 0.01 to 20 molar equivalent of sodium carbonate or sodium hydrogen carbonate is used per the 5-chloropyridine compound.

[10] The method for producing a 5-alkynyl pyridine compound according to any one of the above [1] to [9], wherein from 0.00001 to 1 molar equivalent of the palladium catalyst having phosphine ligands is present per the 5-chloropyridine compound.

[11] The method for producing a 5-alkynyl pyridine compound according to any one of the above [1] to [10], wherein from 0.000001 to 1 molar equivalent of the copper catalyst is present per the 5-chloropyridine compound.

[12] The method for producing a 5-alkynyl pyridine compound according to any one of the above [1] to [11], wherein the solvent is an aprotic polar solvent.

[13] The method for producing a 5-alkynyl pyridine compound according to the above [12], wherein the aprotic polar solvent is at least one selected from the group consisting of dimethylformamide, dimethylacetamide and dimethylsulfoxide.

[14] The method for producing a 5-alkynyl pyridine compound according to any one of the above [1] to [13], wherein the reaction temperature is from 100° C. to 150° C.

[15] The method for producing a 5-alkynyl pyridine compound according to any one of the above [1] to [14], wherein R in the formula 2 and the formula 3 is cyclopropyl.

Advantageous Effects of Invention

The present invention provides an industrial method for producing a 5-alkynyl pyridine compound which is useful as an agricultural and pharmaceutical chemical or as an intermediate thereof at a high yield. Specifically, the desired product of the 5-alkynyl pyridine compound can be produced at a high conversion ratio, a high selectivity to suppress the formation of byproducts and a high yield, as compared with conventional production methods.

DESCRIPTION OF EMBODIMENTS

The 5-chloropyridine compound represented by the formula (1) (also referred to as "compound (1)") and the 5-alkynyl pyridine compound represented by the formula (3) (also referred to as "compound (3)") in the present invention have geometrical isomers of E-isomer and Z-isomer derived from the oxime structure, and the mixing ratio of the geometrical isomers of the compound (1) and the mixing ratio of the geometrical isomers of the compound (3) used in the present invention are E-isomer/Z-isomer=10/90 to 0/100, preferably from 5/95 to 0/100, more preferably 0/100. The mixing ratio of the E-isomer to the Z-isomer can be quantitatively analyzed and calculated by an optional measuring method such as high performance liquid chromatography, gas chromatography or nuclear magnetic resonance spectrum.

In a case where the compound of the present invention or a compound to be used as a starting material in the production method has one, two or more asymmetric carbon atoms, the present invention includes all optically active substances, racemic forms and diastereomers.

In the present specification, "n-" means "normal", "i-" means "iso", "s-" means "secondary", "tert-" or "t-" means "tertiary", "o-" means "ortho", "m-" means "meths", and "p-" means "para".

In the present specification, the expression "$C_a$-$C_b$ alkyl" represents a linear or branched hydrocarbon group containing from a to b carbon atoms, and may, for example, be a methyl group, an ethyl group, a n-propyl group, an i-propyl group, a n-butyl group, an i-butyl group, a t-butyl group, a s-butyl group, a n-pentyl group, a 1-methylbutyl group, a 2-methylbutyl group, a 3-methylbutyl group, a 1-ethylpropyl group, a 1,1-dimethylpropyl group, a 1,2-dimethylpropyl group, a neopentyl group, a n-hexyl group, a 1-methylpentyl group, a 2-methylpentyl group, a 3-methylpentyl group, a 4-methylpentyl group, a 1-ethylbutyl group, a 2-ethylbutyl group, a 1,1-dimethylbutyl group, a 1,2-dimethylbutyl group, a 1,3-dimethylbutyl group, a 2,2-dimethylbutyl group, a 2,3-dimethylbutyl group, a 3,3-dimethylbutyl group, a 1,1,2-trimethylpropyl group, a 1-ethyl-1-methylpropyl group or a 1-ethyl-2-methylpropyl group, and it is selected in the range of the specified number of carbon atoms.

In the present specification, the expression "$C_a$-$C_b$ cycloalkyl" represents a cyclic hydrocarbon group containing from a to b carbon atoms, and may, for example, be a cyclopropyl group, a cyclobutyl group, a 1-methylcyclopropyl group, a 2-methylcyclopropyl group, a cyclopentyl group, a 1-methylcyclobutyl group, a 2-methylcyclobutyl group, a 3-methylcyclobutyl group, a 1-ethylcyclopropyl group, a 2-ethylcyclopropyl group, a 2,2-dimethylcyclopropyl group, a cyclohexyl group, a 1-methylcyclopentyl group, a 2-methylcyclopentyl group, a 3-methylcyclopentyl group, a 2,3-dimethylcyclobutyl group, a 3,3-dimethylcyclobutyl group, a cycloheptyl group, a 1-methylcyclohexyl group, a 2-methylcyclohexyl group, a 3-methylcyclohexyl group, a 4-methylcyclohexyl group, a 2-ethylcyclopentyl group, a 3-ethylcyclopentyl group, a 2,3-dimethylcyclopentyl group or a 2,4-dimethylcyclopentyl group, and it is selected in the range of the specific number of carbon atoms.

Now, the method for producing the compound (3) in the present invention will be described.

The compound (3) may be produced by the reaction shown in the following reaction scheme 1 (hereinafter also referred to as "present reaction").

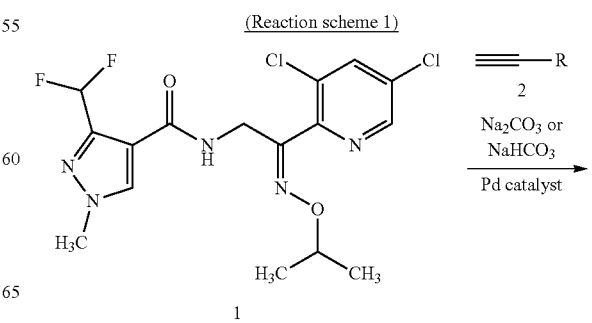

-continued

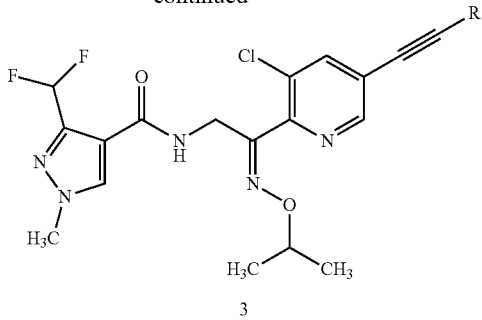

3

In the formula, R is the same as defined above.

The compound (1) and the alkyne compound represented by the formula (2) (hereinafter also referred to as "compound (2)") are reacted by using sodium carbonate or sodium hydrogen carbonate in a solvent in the presence of a palladium catalyst having phosphine ligands, and as a case requires in the presence of a palladium catalyst having phosphine ligands and a copper catalyst, to produce the compound (3).

Sodium carbonate and sodium hydrogen carbonate used in the present invention may be materials to be sodium carbonate and/or sodium hydrogen carbonate respectively under reaction conditions.

The amount of sodium carbonate or sodium hydrogen carbonate to be used in the reaction is at most 20 molar equivalent, preferably at most 10 molar equivalent, more preferably at most 5 molar equivalent, per the compound (1). Further, the amount is at least 0.01 molar equivalent, preferably at least 0.1 molar equivalent, more preferably at least 1 molar equivalent, per the compound (1). As the range of the amount of sodium carbonate or sodium hydrogen carbonate to be used, the above mentioned upper limit value and lower limit value may be optionally combined.

The palladium catalyst having phosphine ligands to be used in the reaction may, for example, be tetrakis(triphenylphosphine)palladium(0), bis(tri-t-butylphosphine)palladium(0), bis(tricyclohexylphosphine)palladium(0), bis[1,2-bis(diphenylphosphino)ethane]palladium(0), bis(tricyclohexylphosphine)palladium(0), dichlorobis(triphenylphosphine)palladium(II), bis(triphenylphosphine)palladium(II) diacetate, dichloro[1,2-bis(diphenylphosphino)ethane]palladium(II), dichloro[1,1'-bis(diphenylphosphino)ferrocene]palladium(II), dichloro[1,3-bis(diphenylphosphino)propane]palladium(II) or dichlorobis(tri-o-tolylphosphine)palladium(II). Preferably, dichlorobis(triphenylphosphine)palladium(II) may be mentioned.

In the reaction, a complex formed by mixing a catalyst precursor and phosphine ligands may be used as a palladium catalyst having phosphine ligands. The complex can be prepared in the reaction system, and as a case requires, the complex may be separately prepared and added to the reaction system.

The catalyst precursor to be used in the reaction may, for example, be dichlorobis(acetonitrile)palladium(II), dichlorodiaminepalladium(II), dichlorobis(benzonitrile)palladium(II), dichloro(1,5-cyclooctadiene)palladium(II), allylpalladium(II) chloride dimer, bis(2-methylallyl)palladium(II) chloride dimer, bis(dibenzylideneacetone)palladium(0), tris(dibenzylideneacetone) (chloroform)dipalladium(0), acetylacetone palladium(II), palladium(II) acetate, palladium(II) trifluoroacetate, palladium(II) trifluoromethanesulfonate, palladium(II) chloride or palladium on carbon. Preferably, palladium(II) chloride or palladium(II) acetate may be mentioned. More preferably, palladium(II) acetate may be mentioned.

The phosphine ligand to be used in the reaction may, for example, be trimethylphosphine, tri-n-butylphosphine, tri-t-butylphosphine, triethoxyphosphine, triphenylphosphine, tris(p-tolyl)phosphine, tris(4-methoxyphenyl)phosphine, 1,2-bis(diphenylphosphino)ethane, 1,2-bis(diphenylphosphino)propane, 1,3-bis(diphenylphosphino)propane, 1,4-bis(diphenylphosphino)butane, 2,2'-bis(diphenylphosphino)-1,1'-binaphthyl, 1,1'-bis(diphenylphosphino)ferrocene or 4,5-bis(diphenylphosphino)-9,9-dimethylxanthene. Preferably, triphenylphosphine, 1,3-bis(diphenylphosphino)propane, 1,4-bis(diphenylphosphino)butane, 1,1'-bis(diphenylphosphino)ferrocene or 4,5-bis(diphenylphosphino)-9,9-dimethylxanthene may be mentioned. More preferably, 4,5-bis(diphenylphosphino)-9,9-dimethylxanthene may be mentioned.

The amount of the phosphine ligands to be used is at most 10 molar equivalent, preferably at most 5 molar equivalent, more preferably at most 3 molar equivalent, per the catalyst precursor. Further, the amount is at least 0.01 molar equivalent, preferably at least 0.1 molar equivalent, more preferably at least 1 molar equivalent, per the catalyst precursor. As the range of the amount of the phosphine ligands to be used, the above mentioned upper limit value and lower limit value may be optionally combined.

The amount of the palladium catalyst having phosphine ligands is at most 1 molar equivalent, preferably at most 0.1 molar equivalent, more preferably at most 0.01 molar equivalent, per the compound (1). Further, the amount is at least 0.000001 molar equivalent, preferably at least 0.00001 molar equivalent, more preferably at least 0.0001 molar equivalent, per the compound (1). As the range of the amount of the palladium catalyst having phosphine ligands to be used, the above mentioned upper limit value and lower limit value may be optionally combined.

The copper catalyst to be used in the reaction may, for example, be copper(I) chloride, copper(I) bromide, copper(I) iodide or copper(I) acetate, and is preferably copper(I) iodide. The amount of the copper catalyst to be used is at most 10 molar equivalent, preferably at most 1 molar equivalent, more preferably at most 0.1 molar equivalent, per the compound (1). Further, the amount is at least 0.00001 molar equivalent, preferably at least 0.0001 molar equivalent, more preferably at least 0.001 molar equivalent, per the compound (1). As the range of the amount of the copper catalyst to be used, the above mentioned upper limit value and lower limit value may be optionally combined.

The compound (1) to be used in the reaction is a known compound and may, for example, be synthesized in accordance with the method described in Patent Document 2.

Further, in general, in a case where an oxime compound is synthesize, the oxime compound is obtained as a mixture of geometrical isomers of E-isomer and Z-isomer in many cases, and a method of converting the mixture of geometrical isomers of the oxime compound into E-isomer or Z-isomer is known. For example, a method of applying light described in Patent Document 2, a method of using an acidic compound described in JP-A-H10-195064, etc. are known.

Some of the compound (2) to be used in the reaction are known compounds, and some of them are commercially available. Further, the others can be synthesized in accordance with known methods disclosed in literatures, for example, by a method of dehalogenation of a dihaloalkene compound described in Tetrahedron, 1998, vol. 54, issue 7, pp. 1021 or Journal of Organometallic Chemistry, 2007, vol. 692, issue 18, pp. 3892, a method of dehydrohalogenation of a dihaloalkane described in Tetrahedron Letters, 2012, vol. 53, issue 18, pp. 2295, a method of desorbing trifluoromethanesulfonic acid from an alkenyl triflate compound described in Journal of Organic Chemistry, 1974, vol. 39, issue 4, pp. 581, a method of reacting a trimethylsilylacetylene compound and an alkyl halide described in Journal of American Chemical Society, 1970, vol. 92, issue 21, pp. 6314 or Tetrahedron Letters, 2001, vol. 42, issue 41, pp. 7211 or the like.

The amount of the compound (2) to be used is at most 20 molar equivalent, preferably at most 10 molar equivalent, more preferably at most 5 molar equivalent and at least 0.01 molar equivalent, preferably at least 0.1 molar equivalent, more preferably at least 1 molar equivalent per the compound (1). As the range of the compound (2) to be used, the above mentioned upper limit value and lower limit value may be optionally combined.

The reaction temperature is usually from 50 to 200° C., preferably from 100 to 150° C.

The reaction time varies depending on the concentration of reaction substrates and the reaction temperature, however, it is usually from 1 minute to 100 hours, preferably from 10 minutes to 72 hours, more preferably from 1 hour to 48 hours.

The solvent to be used in the reaction is not particularly restricted, so far as the proceeding of the reaction is not impaired. An aprotic solvent, for example, such as an ether solvent such as diethyl ether, tetrahydrofuran, cyclopentyl methyl ether or tertiary butyl methyl ether, an ester solvent such as methyl acetate, ethyl acetate, butyl acetate or methyl propionate, an amide solvent such as N,N-dimethylformamide, N,N-dimethylacetamide or N-methylpyrrolidone, a nitrile solvent such as acetonitrile or propionitrile, a ketone solvent such as methyl ethyl ketone or methyl isobutyl ketone, or dimethylsulfoxide may be mentioned. The amide solvent or dimethylsulfoxide is preferably mentioned, and N,N-dimethylformamide, N,N-dimethylacetamide or dimethylsulfoxide is more preferably mentioned. Two or more of these solvents may be mixed for use. Further, the reaction may be carried out in the absence of a solvent, so long as the proceeding of the reaction is not impaired.

As a case required, the reaction may be carried out under an inert gas atmosphere of e.g. nitrogen or argon.

In the reaction, a mixture after the termination of the reaction may be subjected to an ordinal post treatment such as direct concentration, a procedure such that the reaction mixture is dissolved in an organic solvent and washed with water and then, an organic layer to be obtained is concentrated or a procedure such that the reaction mixture is poured into ice water, extracted with an organic solvent, and then an organic layer to be obtained is concentrated, to obtain the desired compound. Further, if purification is necessary, the desired compound may be isolated or purified by an optional purification method such as recrystallization, fractionation by column chromatography, thin layer chromatography or liquid chromatography or distillation.

EXAMPLES

Now, the present invention will be described in further detail with reference to Synthetic Examples of the present invention. However, the present invention is by no means restricted thereto.

Quantitative analysis described in Examples and Reference Examples is quantitative analysis by an internal standard method by means of high performance liquid chromatography (hereinafter referred to as "HPLC") and was carried out under the following analytical conditions.

[HPLC Analytical Conditions]

Column: Inertsil ODS-SP 250 mm 4.6 mmφ 5 µm (manufactured by GL Science Inc.),

Flow rate: 1 mL/min,

Eluent: acetonitrile/0.1% trifluoroacetic acid aqueous solution=3/2 (volume ratio), UV detection wavelength: 254 nm Internal standard substance: 4-t-butyl biphenyl Further, the chemical shift values of proton nuclear magnetic resonance spectra (hereinafter referred to as "$^1$H-NMR") mentioned in Examples were measured by using Me$_4$Si (tetramethylsilane) as the standard substance in a deuterated chloroform solvent at 300 Hz (apparatus: JNM-ECX300, manufactured by JEOL Ltd).

Among symbols of chemical shift values of $^1$H-NMR, "s" means "singlet", "d" means "doublet", "t" means "triplet", and "m" means "multiplet" respectively.

Reference Example 1

Preparation of Compound (1)

168 g of (EZ)—N-[2-(3,5-dichloropyridin-2-yl)-2-(isopropoxyimino)ethyl]-3-(difluoromethyl)-1-methyl-1H-pyrazole-4-carboxamide (Z isomer/E isomer=15.2/84.8) prepared in accordance with the known method described in Patent Document 2 and 672 g of ethyl acetate were mixed at room temperature, and 20 mL of an ethyl acetate solution of hydrogen chloride (4.5 mass %, manufactured by Tokyo Chemical Industry Co., Ltd.) (0.056 equivalent as hydrogen chloride) was added to the mixed solution at 35° C. The mixed solution was stirred at the same temperature for 1 hour, and then the solvent was distilled off under reduced pressure.

Ethyl acetate was added to the obtained residue at room temperature to prepare 420 g of an ethyl acetate solution. 20 mL of an ethyl acetate solution of hydrogen chloride (4.5 mass %, manufactured by Tokyo Chemical Industry Co., Ltd.) (0.056 equivalent as hydrogen chloride) was added to the ethyl acetate solution at 35° C. 252 g of n-heptane was dropwise added to the reaction solution at the same temperature over 1 hour, and as a result, precipitation of crystals was observed. After the termination of the dropwise addition of n-heptane, the reaction mixture was stirred at the same temperature for 1 hour. After the termination of stirring, 252 g of n-heptane was dropwise added thereto over 1 hour, and the reaction mixture was stirred at the same temperature for 1 hour. After the termination of stirring, 252 g of n-heptane was further dropwise added thereto over 1 hour, and the reaction mixture was stirred at the same temperature for 1 hour. Then, the reaction mixture was stirred at room temperature for 24 hours. Precipitated crystals were collected by filtration, and the obtained crystals were washed with a mixed solution of 268.8 g of n-heptane and 67.2 g of ethyl acetate to obtain 144.5 g of the desired product as pale yellow crystals (yield: 86.0%).

Based on the relationship of the retention time of Z-isomer and E-isomer obtained in accordance with Patent Document 2 at Synthetic Example 2, step 7, the retention time by HPLC of compound No. 17-011 mentioned in Patent Document 2 and the crystals obtained in the above Reference Example 1 were compared. As a result, the area ratio of the Z-isomer of the compound (1) to the E-isomer of the compound (1) was 98.2/1.8, and the sum of the relative area percentages of the two peaks was 98.6%.

Examples 1-1 and 1-2 and Reference Examples 2-1 to 2-4

Preparation of (Z)—N-[2-[3-chloro-5-(cyclopropylethynyl)pyridin-2-yl]-2-(isopropoxyimino)ethyl]-3-(difluoromethyl)-1-methyl-1H-pyrazole-4-carboxamide (Hereinafter Referred to as Compound (3-1))

1.20 g of the compound (1), 0.45 g (1.5 equivalent) of sodium carbonate, 3 mg of copper(I) iodide, 15 mg of triphenylphosphine, 10 mg of bis(triphenylphosphine)palladium(II) chloride, 0.28 g of cyclopropylacetylene and 2.0 mL of dimethylsulfoxide were added in a high-pressure tube (manufactured by ACE GLASS INC.), followed by stirring for 24 hours under a nitrogen atmosphere at 110° C. After the termination of the reaction, the reaction mixture was cooled to 40° C. and diluted with 10 mL of dimethylsulfoxide, 50 mL of acetonitrile and 40 mL of water to obtain 114.33 g of an acetonitrile solution containing the desired product. The acetonitrile solution was quantitatively analyzed, and as a result, the acetonitrile solution contained 0.92 g of the desired product (yield: 71.6%).

Further, reactions were carried out under the same conditions as described above, except that the type of the base was changed. The type of the base, the amount of the base (1.5 equivalent per the compound (1) in all cases) and the yield are shown in the following Table 1.

TABLE 1

| Example No | Base | Amount | Yield(%) |
|---|---|---|---|
| Example 1-1 | Sodium carbonate | 0.45 g | 71.6 |
| Example 1-2 | Sodium hydrogen carbonate | 0.36 g | 61.9 |
| Reference Example 2-1 | Potassium carbonate | 0.59 g | 12.7 |
| Reference Example 2-2 | Sodium acetate | 0.35 g | 12.5 |
| Reference Example 2-3 | Ammonium carbonate | 0.41 g | 9.6 |
| Reference Example 2-4 | 28 mass % Ammonium aqueous solution | 0.26 g | 39.2 |

Examples 2-1 and 2-2

Preparation of Compound (3-1)

A mixed solution of 0.13 g of palladium(II) acetate, 0.11 g of copper(I) iodide and 20 mL of dimethylsulfoxide was stirred for 30 minutes under a nitrogen atmosphere at room temperature to obtain a blackish brown transparent solution. 1.20 g of the compound (1), 0.45 g of sodium carbonate, 24 mg of 1,4-bis(diphenylphosphino)butane, 0.28 g of cyclopropylacetylene and 1.0 mL of dimethylsulfoxide were added in a high-pressure tube (manufactured by ACE GLASS INC.). Further, 1.0 mL of the blackish brown transparent solution was added thereto, followed by stirring for 24 hours under a nitrogen atmosphere at 110° C. After the termination of the reaction, the reaction mixture was cooled to 40° C., and diluted with 1 mL of dimethylsulfoxide, 5 mL of acetonitrile and 4 mL of water to obtain 15.56 g of an acetonitrile solution containing the desired product. The acetonitrile solution was quantitatively analyzed, and as a result, the acetonitrile solution contained 0.81 g of the desired product (yield 63.3%).

Reactions were carried out under the same conditions as described above, except that the type of the ligand was changed. The type of the ligand, the amount of the ligand (0.02 equivalent per the compound (1) in all cases) and the yield are shown in the following Table 2. Further, in Table, "1,4-bis(diphenylphosphino)butane" is represented as "dppb", and "4,5-bis(diphenylphosphino)-9,9-dimethylxanthene" is represented as "Xantphos".

TABLE 2

| Example No | Ligand | Amount | Yield (%) |
|---|---|---|---|
| Example 2-1 | dppb | 24 mg | 63.3 |
| Example 2-2 | Xantphos | 33 mg | 91.4 |

Examples 3-1 to 3-3

Preparation of Compound (3-1)

A mixed solution of 0.13 g of palladium(II) acetate, 0.11 g of copper(I) iodide and 40 mL of dimethylsulfoxide was stirred for 30 minutes under a nitrogen atmosphere at room temperature to obtain a blackish brown transparent solution. 1.20 g of the compound (1), 0.45 g of sodium carbonate, 8 mg of 4,5-bis(diphenylphosphino)-9,9-dimethylxanthene, 0.28 g of cyclopropylacetylene and 1.0 mL of dimethylsulfoxide were added in a high-pressure tube (manufactured by ACE GLASS, INC.). Further, 1.0 mL of the blackish brown transparent solution was added thereto, followed by stirring for 24 hours under a nitrogen atmosphere at 110° C. After the termination of the reaction, the reaction mixture was cooled to 40° C. and diluted with 10 mL of dimethylsulfoxide, 50 mL of acetonitrile and 40 mL of water to obtain 96.28 g of an acetonitrile solution containing the desired product. The acetonitrile solution was quantitatively analyzed, and as a result, the acetonitrile solution contained 1.14 g of the desired product (yield: 88.0%).

Further, reactions were carried out under the same conditions as described above, except that the amounts of palladium(II) acetate, copper(I) iodide and 4,5-bis(diphenylphosphino)-9,9-dimethylxanthene were changed. The amounts of the respective reagents and the yield of the desired product are shown in the following Table 3. Further, the yield of the desired product was calculated in accordance with the method described in Example 3. Further, in Table, "4,5-bis(diphenylphosphino)-9,9-dimethylxanthene" is represented as "Xantphos".

TABLE 3

| Example No | Palladium acetate | Copper iodide | Xantphos | Yield (%) |
|---|---|---|---|---|
| Example 3-1 | 0.13 g | 0.11 g | 8 mg | 88.0 |
| Example 3-2 | 0.13 g | 0 g | 8 mg | 75.5 |
| Example 3-3 | 0.13 g | 0.11 g | 4 mg | 90.1 |

Example 4

Preparation of Compound (3-1)

2.41 g of the compound (1), 0.91 g of sodium carbonate, 8 mg of 4,5-bis(diphenylphosphino)-9,9-dimethylxanthene, 3 mg of copper(I) iodide and 3.7 g of dimethylsulfoxide were added in a high-pressure tube (manufactured by ACE GLASS, INC.). Further, 0.57 g of cyclopropylacetylene and 1.0 mL of a dimethylsulfoxide solution of 14.3 mmol/L of palladium(II) acetate were added thereto, followed by stirring for 24 hours under a nitrogen atmosphere at 110° C. After the termination of the reaction, the reaction mixture was cooled to 40° C. and diluted with 10 mL of dimethylsulfoxide, 50 mL of acetonitrile and 40 mL of water to obtain 119.73 g of an acetonitrile solution containing the desired product. The acetonitrile solution was quantitatively analyzed, and as a result, the acetonitrile solution contained 2.32 g of the desired product (yield: 90.0%).

Examples 5-1 to 5-3

Preparation of Compound (3-1)

2.40 g of the compound (1), 0.91 g of sodium carbonate, 11 mg of copper(I) [4,5-bis(dimethylphosphino)-9,9-dimethylxanthene] iodide and 3.7 g of dimethylsulfoxide were added in a high-pressure tube (manufactured by ACE GLASS, INC.). Further, 0.57 g of cyclopropylacetylene and 1.0 mL of a dimethylsulfoxide solution of 14.3 mmol/L palladium(II) acetate were added thereto, followed by stirring for 24 hours under a nitrogen atmosphere at 110° C. After the termination of the reaction, the reaction mixture was cooled to 40° C. and diluted with 10 mL of dimethylsulfoxide, 50 mL of acetonitrile and 40 mL of water to obtain 148.04 g of an acetonitrile solution containing the desired product. The acetonitrile solution was quantitatively analyzed, and as a result, the acetonitrile solution contained 2.34 g of the desired product (yield: 91.1%).

Reactions were carried out under the same conditions, except that the reaction solvent was changed. The type of the solvent, the amount of the solvent and the yield of the desired product are shown in the following Table 4.

TABLE 4

| Example No | Solvent | Amount | Yield (%) |
| --- | --- | --- | --- |
| Example 5-1 | Dimethylsulfoxide | 3.7 g | 91.1 |
| Example 5-2 | N,N-Dimethylformamide | 3.7 g | 90.3 |
| Example 5-3 | N,N-Dimethylacetamide | 3.7 g | 89.9 |

Examples 6-1 to 6-3

Preparation of Compound (3-1)

A mixed solution of 83 mg of 4,5-bis(diphenylphosphino)-9,9-dimethylxanthene, 27 mg of copper(I) iodide and 10 mL of dimethylsulfoxide was stirred for 30 minutes under a nitrogen atmosphere at room temperature to obtain a colorless transparent solution. 2.40 g of the compound (1), 0.58 g of sodium hydrogen carbonate, 0.57 g of cyclopropylacetylene and 2.6 g of dimethylsulfoxide were added in a high-pressure tube manufactured by ACE GLASS, INC.). Further, 1.0 mL of the colorless transparent solution was added thereto. Further, 1.0 mL of a dimethylsulfoxide solution of 5.7 mmol/L palladium(II) acetate was added thereto, followed by stirring for 24 hours under a nitrogen atmosphere at 110° C. After the termination of the reaction, the reaction mixture was cooled to 40° C., diluted with 2.4 mL of water and extracted with 8.3 mL of toluene. The obtained organic layer was washed with water (2.4 mL×2 times), and then 33.08 g of a toluene solution containing the desired product was obtained. The toluene solution was quantitatively analyzed, and as a result, the toluene solution contained 9.58 g of the desired product (yield: 86.8%).

Reactions were carried out under the same conditions as described above, except that the type of the base and the amount of the base were changed. The type of the base, the amount of the base and the yield of the desired product are shown in the following Table 5.

TABLE 5

| Example No | Base | Amount | Yield (%) |
| --- | --- | --- | --- |
| Example 6-1 | Sodium hydrogen carbonate | 0.58 g | 86.8 |
| Example 6-2 | Sodium carbonate | 0.73 g | 87.3 |
| Example 6-3 | Sodium carbonate | 0.36 g | 82.1 |

Example 7

Preparation of Compound (3-1)

A mixed solution of 104 mg of 4,5-bis(diphenylphosphino)-9,9-dimethylxanthene, 34 mg of copper(I) iodide and 15 mL of dimethylsulfoxide was stirred for 30 minutes under a nitrogen atmosphere at room temperature to obtain a colorless transparent solution. 10.05 g of the compound (1), 2.41 g of sodium hydrogen carbonate and 9.0 g of dimethylsulfoxide were added in an autoclave. Further, 5.0 mL of the colorless transparent solution, 2.05 g of cyclopropylacetylene and 5.0 mL of a dimethylsulfoxide solution of 4.8 mmol/L palladium(II) acetate were added, followed by stirring for 45 hours under a nitrogen atmosphere at 110° C. After the termination of the reaction, the reaction mixture was cooled to 40° C., diluted with 22 mL of water and extracted with toluene (23 mL×2 times). The obtained organic layer was washed with water (20 mL×2 times), and 57.85 g of a toluene solution containing the desired product was obtained. The toluene solution was quantitatively analyzed, and as a result, the toluene solution contained 9.58 g of the desired product (yield: 89.0%).

Reference Examples 3-1 to 3-4

Preparation of Compound (3-1)

0.30 g of (Z)—N-[2-(5-bromo-3-chloropyridin-2-yl)-2-(isopropoxyimino)ethyl]-3-(difluoromethyl)-1-methyl-1H-pyrazole-4-carboxamide, 0.26 g of triethylamine, 18 mg of copper(I) iodide, 23 mg of bis(triphenylphosphino)palladium(II) chloride, 54 mg of cyclopropylacetylene and 5.0 mL of dimethylsulfoxide were added in a high-pressure tube (manufactured by ACE GLASS, INC.), followed by stirring for 1 hour under a nitrogen atmosphere at 50° C. After the termination of the reaction, the reaction mixture was cooled to 30° C. and diluted with 15 mL of acetonitrile and 5 mL of water to obtain 21.17 g of an acetonitrile solution containing the desired product. The acetonitrile solution was quantitatively analyzed, and as a result, the acetonitrile solution contained 0.24 g of the desired product (yield: 82.9%).

Further, reactions were carried out under the same conditions as described above, except that the starting material was changed to 0.27 g of the compound (1). The reaction temperature, the reaction time and the yield of the desired product are shown in the following Table 6.

TABLE 6

| Reference Example No | Reaction temperature | Reaction time | Yield (%) |
|---|---|---|---|
| 3-2 | 50° C. | 1 hour | 0.2 |
| 3-3 | 110° C. | 1 hour | 0.4 |
| 3-4 | 110° C. | 24 hours | 0.5 |

Reference Examples 4-1 to 4-4

Preparation of Compound (3-1)

Reactions were carried out under the same conditions as in Example 3-1, except that the base was changed. The type of base, the amount of the base (1.5 equivalent) and the yield of the desired product are shown in the following Table 7. Further, the yield of the desired product was calculated in accordance with the method described in Example 3. Further, in Table 7, "1,8-diazabicyclo[5,4,0]-7-undecene" is represented as "DBU".

TABLE 7

| Reference Example No | Base | Amount | Yield(%) |
|---|---|---|---|
| 4-1 | Tripotassium phosphate | 0.91 g | 0 |
| 4-2 | 32 mass % Sodium hydroxide aqueous solution | 0.54 g | 0 |
| 4-3 | DBU | 0.65 g | 0 |
| 4-4 | N,N-Diisopropylethylamine | 0.55 g | 13.5 |

Reference Example 5

Preparation of Copper(I) [4,5-Bis(Diphenylphosphino)-9,9-Dimethylxanthene] Iodide A mixed solution of 1.00 g of 4,5-bis(diphenylphosphino)-9,9-dimethylxanthene, 0.30 g of copper(I) iodide and 16 mL of dichloromethane was stirred for 2 hours under a nitrogen atmosphere at room temperature. The solvent was distilled off from the obtained yellow transparent solution under reduced pressure, and the obtained residue was washed with 6 mL of acetonitrile to obtain 1.18 g of the desired product as a white solid.

$^1$H NMR (CDCl$_3$, Me$_4$Si, 300 MHz) δ7.59 (d, J=7.8 Hz, 2H), 7.40-7.45 (m, 8H), 7.32-7.37 (m, 4H), 7.23-7.28 (m, 8H), 7.13 (t, J=7.8 Hz, 2H), 6.60 (m, 2H), 1.66 (s, 6H)

INDUSTRIAL APPLICABILITY

The method for producing a 5-alkynyl pyridine compound according to the present invention is extremely useful for producing an oxime-substituted amide compound having an excellent biological activity, particularly fungicidal activity, or an intermediate thereof.

The entire disclosure of Japanese Patent Application No. 2018-114439 filed on Jun. 15, 2018 including specification, claims and summary is incorporated herein by reference in its entirety.

What is claimed is:

1. A method for producing a 5-alkynyl pyridine compound represented by the formula (3):

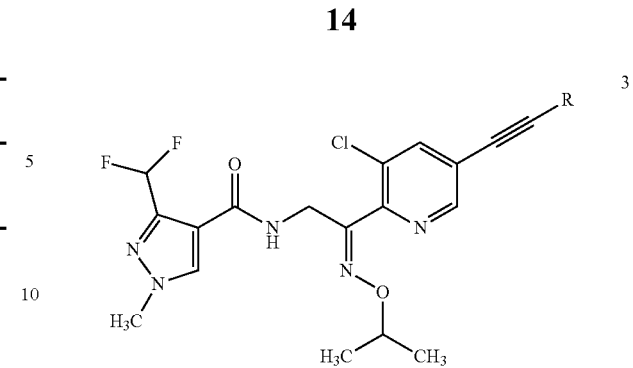

wherein R is a hydrogen atom, a $C_1$-$C_6$ alkyl or a $C_3$-$C_7$ cycloalkyl, which comprises reacting a 5-chloropyridine compound represented by the formula (1):

and an alkyne compound represented by the formula (2):

wherein R is the same as defined above, by using sodium carbonate or sodium hydrogen carbonate in the presence of a palladium catalyst having phosphine ligands in a solvent.

2. The method for producing a 5-alkynyl pyridine compound according to claim 1, wherein the 5-chloropyridine compound and the alkyne compound are reacted in the presence of a copper catalyst and the palladium catalyst having phosphine ligands.

3. The method for producing a 5-alkynyl pyridine compound according to claim 1, wherein the phosphine ligand is 1,4-bis(diphenylphosphino)butane or 4,5-bis(diphenylphosphino)-9,9-dimethylxanthene.

4. The method for producing a 5-alkynyl pyridine compound according to claim 1, wherein the palladium catalyst having phosphine ligands is tetrakis(triphenylphosphine)palladium(0), bis(tri-t-butylphosphine)palladium(0), bis(tricyclohexylphosphine)palladium(0), bis[1,2-bis(diphenylphosphino)ethane]palladium(0), bis(tricyclohexylphosphine)palladium(0), dichlorobis(triphenylphosphine)palladium(II), bis(triphenylphosphine)palladium(II) diacetate, dichloro[1,2-bis(diphenylphosphino)ethane]palladium(II), dichloro[1,1'-bis(diphenylphosphino)ferrocene]palladium(II), dichloro[1,3-bis(diphenylphosphino)propane]palladium(II) or dichlorobis(tri-o-tolylphosphine)palladium(II).

5. The method for producing a 5-alkynyl pyridine compound according to claim 4, wherein the palladium catalyst having phosphine ligands is dichlorobis(triphenylphosphine)palladium(II).

6. The method for producing a 5-alkynyl pyridine compound according to claim 2, wherein the copper catalyst is copper(I) chloride, copper(I) bromide, copper(I) iodide or copper(I) acetate.

7. The method for producing a 5-alkynyl pyridine compound according to claim 6, wherein the copper catalyst is copper(I) iodide.

8. The method for producing a 5-alkynyl pyridine compound according to claim 1, wherein from 0.01 to 20 molar equivalent of the alkyne compound is reacted per the 5-chloropyridine compound.

9. The method for producing a 5-alkynyl pyridine compound according to claim 1, wherein from 0.01 to 20 molar equivalent of sodium carbonate or sodium hydrogen carbonate is used per the 5-chloropyridine compound.

10. The method for producing a 5-alkynyl pyridine compound according to claim 1, wherein from 0.00001 to 1 molar equivalent of the palladium catalyst having phosphine ligands is present per the 5-chloropyridine compound.

11. The method for producing a 5-alkynyl pyridine compound according to claim 1, wherein from 0.000001 to 1 molar equivalent of the copper catalyst is present per the 5-chloropyridine compound.

12. The method for producing a 5-alkynyl pyridine compound according to claim 1, wherein the solvent is an aprotic polar solvent.

13. The method for producing a 5-alkynyl pyridine compound according to claim 12, wherein the aprotic polar solvent is at least one selected from the group consisting of dimethylformamide, dimethylacetamide and dimethylsulfoxide.

14. The method for producing a 5-alkynyl pyridine compound according to claim 1, wherein the reaction temperature is from 100° C. to 150° C.

15. The method for producing a 5-alkynyl pyridine compound according to claim 1, wherein R in the formula 2 and the formula 3 is cyclopropyl.

* * * * *